(12) United States Patent
Yancey et al.

(10) Patent No.: US 11,083,411 B2
(45) Date of Patent: Aug. 10, 2021

(54) SYSTEMS AND METHODS FOR USER MONITORING

(71) Applicant: SDC U.S. SmilePay SPV, Nashville, TN (US)

(72) Inventors: Christopher Yancey, Nashville, TN (US); John Dargis, Nashville, TN (US); Alex Fenkell, Nashville, TN (US)

(73) Assignee: SDC U.S. SmilePay SPV, Nashville, TN (US)

( * ) Notice: Subject to any disclaimer, the term of this patent is extended or adjusted under 35 U.S.C. 154(b) by 0 days.

(21) Appl. No.: 16/563,429

(22) Filed: Sep. 6, 2019

(65) Prior Publication Data

US 2021/0068745 A1    Mar. 11, 2021

(51) Int. Cl.
*A61B 5/00* (2006.01)
*G06T 7/00* (2017.01)
*G16H 20/30* (2018.01)
*G06Q 50/00* (2012.01)
*A61C 7/08* (2006.01)

(52) U.S. Cl.
CPC .............. *A61B 5/4547* (2013.01); *A61C 7/08* (2013.01); *G06Q 50/01* (2013.01); *G06T 7/0012* (2013.01); *G16H 20/30* (2018.01); *G06T 2207/20224* (2013.01); *G06T 2207/30036* (2013.01)

(58) Field of Classification Search
CPC ...... A61B 5/4547; G16H 20/30; G06Q 50/01; A61C 7/08; G06T 7/0012; G06T 2207/20224; G06T 2207/30036
See application file for complete search history.

(56) References Cited

U.S. PATENT DOCUMENTS

| | | | | |
|---|---|---|---|---|
| 2002/0102009 A1* | 8/2002 | Jones | ........................ | A61C 9/00 382/100 |
| 2010/0260405 A1* | 10/2010 | Cinader, Jr. | .............. | A61C 7/00 382/131 |
| 2014/0229192 A1* | 8/2014 | Zastrow | ............... | A61B 5/0022 705/2 |
| 2014/0335469 A1* | 11/2014 | Boyden | .................... | A61B 7/04 433/27 |
| 2016/0374785 A1* | 12/2016 | Fridzon | .................. | A61B 90/37 705/2 |
| 2018/0077105 A1* | 3/2018 | DeGraide | .............. | H04L 51/063 |
| 2020/0000551 A1* | 1/2020 | Li | ........................... | G16H 50/50 |
| 2020/0066391 A1* | 2/2020 | Sachdeva | .................. | A61C 5/30 |

* cited by examiner

*Primary Examiner* — John W Lee
(74) *Attorney, Agent, or Firm* — Foley & Lardner LLP

(57) ABSTRACT

A monitoring system includes a communications circuit and an analysis circuit where the communications circuit is configured to receive an image of a user from a social media system and receive orthodontic treatment plan data associated with the user from an aligner fabrication computer system. The analysis circuit is configured to determine an actual oral condition of the user at a time when the image of the user was taken, determine an expected oral condition of the user at the time when the image of the user was taken based on the orthodontic treatment plan data, compare the actual oral condition and the expected oral condition, and generate an output based on the comparison. The communications system communications the output to at least one of the user device and the aligner fabrication computer system.

23 Claims, 7 Drawing Sheets

SYSTEMS AND METHODS FOR USER MONITORING

BACKGROUND

This application relates generally to the field of user monitoring. More specifically, this application relates to using three-dimensional oral scans and two-dimensional images of a user to monitor an orthodontic condition, oral health, and smile characteristics of a user.

Dental aligners are plastic trays custom made to fit tightly over the teeth of a user to force the teeth to move to a desired location. Dental aligners are fabricated based on a three-dimensional model of the user's teeth. A plurality of dental aligners may be provided to the user to move the teeth from an initial position to a final position over time. To move the teeth effectively, the user must wear the aligners for a specified amount of time per day. If the user does not wear the aligners for the specified amount of time per day (e.g., due to lack of motivation, the aligners not fitting properly, a broken aligner, etc.), the user's teeth may not move at the desired rate.

Monitoring the progress of an orthodontic condition or the oral health of a user is desirable to notify the user and the medical provider of the progress of a prescribed treatment, the evolution of smile confidence, and changing oral health of the user. Monitoring and providing feedback to the user and medical provider can inform the user and the medical provider regarding treatment status and of any potential complications.

SUMMARY

An embodiment relates to a monitoring system. The monitoring system includes a communications circuit and an analysis circuit. The communications circuit is configured to receive an image of a user from a social media system, and to receive orthodontic treatment plan data associated with the user from an aligner fabrication computer system. The analysis circuit is configured to determine an actual oral condition of the user at a time when the image of the user was taken, determine an expected oral condition of the user at the time when the image of the user was taken based on the orthodontic treatment plan data, compare the actual oral condition and the expected oral condition, and generate an output based on the comparison. The communications circuit is further configured to communicate the output to at least one of the user device and the aligner fabrication computer system.

Another embodiment relates to a method. The method includes receiving, by a communications circuit, an image of a user from a social media system. The method also includes receiving, by the communications circuit, orthodontic treatment plan data associated with the user from an aligner fabrication computer system. The method also includes determining, by an analysis circuit, an actual oral condition of the user at a time when the image of the user was taken. The method also includes determining, by the analysis circuit, an expected oral condition of the user at the time when the image of the user was taken based on the orthodontic treatment plan data. The method also includes comparing, by the analysis circuit, the actual oral condition and the expected oral condition. The method also includes generating, by the analysis circuit, an output based on the comparison. The method also includes communicating, by the communications circuit, the output to at least one of the user device and the aligner fabrication computer system.

Another embodiment relates to a method. The method includes receiving, by a communications circuit, image data of a user from a social media system, where the image data comprises a plurality of images of a smile of the user undergoing an orthodontic treatment plan configured to move one or more teeth of the user. The method also includes determining, by an analysis circuit, a smile characteristic of the user based on the plurality of images. The method also includes communicating, by the communications circuit, an output comprising the smile characteristic to at least one of a user device associated with the user and an aligner fabrication computer system.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

When a user desires to move his/her teeth from an initial configuration to a corrected configuration, the initial configuration is generally captured in three-dimensions using a three-dimensional ("3D") scanning device (e.g., either from a dental impression or from directly scanning the teeth of the user). A treatment plan is created based on the initial configuration and a desired final configuration, and one or more sets of aligners are fabricated and provided to the user, along with instructions as to how and when to wear the aligners. However, the user may not wear the aligners according to the instructions, and may need to be reminded of his/her progress toward the final tooth configuration to motivate the user to adhere to the instructions. In some embodiments, the systems and methods herein may provide motivation to the user to gamify the process of orthodontic treatment based on a user desire to complete the treatment and achieve the desired tooth configuration to "win". In some embodiments, the user's progress can be tracked and displayed to the user in comparison to other users (e.g., an average user, by other similarly situated users, by geographic location such as country, state, city, or zip code). In some embodiments, the user may be awarded icons or "badges" for completing certain milestones in treatment (e.g., for a tooth being moved a threshold distance, for completing a certain percentage of the treatment plan, for wearing aligners as recommended for a threshold period of time or a threshold number of days, weeks, or months). In some cases, the teeth of the user may not move as expected according to the treatment plan. Additionally, the user may wear the aligners according to the instructions but may desire to view his/her progress toward the final tooth configuration. The user may also desire to view a status of the dental and/or oral health of the user.

Figure 1:
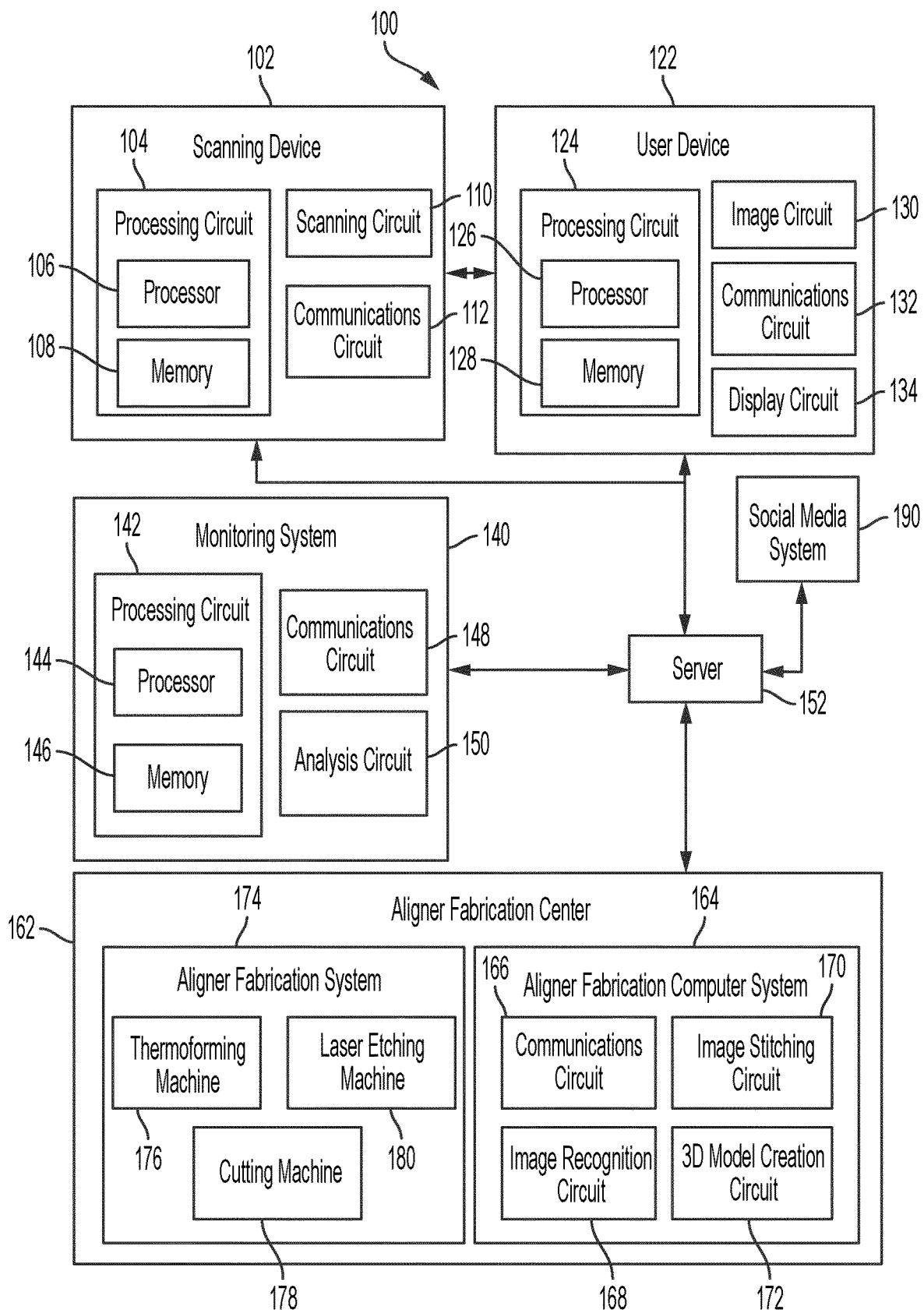
FIG. 1 is a block diagram of a system for monitoring an orthodontic condition, according to some embodiments.

Referring to FIG. 1, a block diagram of a system 100 for monitoring an orthodontic condition is shown, according to some embodiments. The system 100 includes a scanning device 102, a user device 122, a monitoring system 140, a server 152, an aligner fabrication center 162, and a social media system 190.

The scanning device 102 can be any device configured to scan a 3D surface. Examples of the scanning device 102 include, but are not limited to, non-contact active 3D scanners (e.g., time-of-flight, triangulation, conoscopic holography, infrared, visible light projectors, pattern projecting lights, or any other kind of non-contact active 3D scanner), hand held laser 3D scanners, structured light 3D scanners, modulated light 3D scanners, and non-contact passive 3D scanners (e.g., stereoscopic, photometric, silhouette, or any other kind of non-contact passive 3D scanner). In some embodiments, the scanning device 102 is an at-home 3D scanner that can be operated by the user.

The scanning device 102 includes a processing circuit 104, a scanning circuit 110, and a communications circuit 112. The processing circuit 104 is further shown to include a processor 106 and a memory 108. The processor 106 can be any type of processor capable of performing the functions described herein. The processor 106 may be a single or multi-core processor(s), digital signal processor, microcontroller, or other processor or processing/controlling circuit. Similarly, the memory 108 can be any type of volatile or non-volatile memory or data storage capable of performing the functions described herein. In operation, the memory 108 may store various data and software used during operation of the scanning device 102, such as operating systems, applications, programs, libraries, and drivers. The memory 108 is communicatively coupled to the processor 106 such that the processor 106 can execute files located in the memory 108. As will be discussed herein, processing can include computing on the scanning device 102, on a user device 122 (e.g., a mobile device), or the server 152 (e.g., a remote server).

The scanning circuit 110 is communicably coupled to the processor 106 and is configured to conduct a scan of one or more objects. In this regard, the scanning circuit 110 gathers images of the object(s) being scanned (e.g., the size, shape, color, depth, tracking distance, and other physical characteristics) such that the data can be provided to other circuits in the scanning device 102 (e.g., the communications circuit 112). To appropriately scan the target objects, the scanning circuit 110 can include a wide variety of sensors including, but not limited to, gyroscopes, accelerometers, magnetometers, inertial measurement units ("IMU"), depth sensors, pattern projectors, and color sensors.

The communications circuit 112 is communicably coupled to the scanning circuit 110 and is configured to send communications to, and receive communications from, the user device 122 and the server 152. For example, the communications circuit 112 can communicate the scan data to the server 152. As another example, the communications circuit 112 can provide the scan data to the user device 122 for the user device 122 to send to the server 152. Additionally, the communications circuit 112 can provide the scan data to the user device 122 for the user device to display images of the scan in real time to the user during the scan. The communications circuit 112 can communicate with the user device 122 and the server 152 in a variety of ways including, but not limited to, Bluetooth, a WiFi network, a wired local area network (LAN), Zigbee, a wired direct connection between the user device 122 and the scanning device 102, or any other suitable way for devices to exchange information.

The user device 122 can be any type of portable device configured to run a mobile application ("application"). As used herein, the term "application" refers to software that can be loaded on to a piece of hardware (e.g., the user device 122), where the software communicates with both the hardware and a server to perform the desired functions. Examples of the user device 122 include, but are not limited to, a mobile phone, a tablet computer, a laptop computer, a smart watch, a fitness tracker, and any other Internet-connected device that is capable of running an application.

The user device 122 is shown to include a processing circuit 124, an image circuit 130, a communications circuit 132, and a display circuit 134. The processing circuit 124 is further shown to include a processor 126 and a memory 128. The processor 126 can be any type of processor capable of performing the functions described herein. The processor 126 may be a single or multi-core processor(s), digital signal processor, microcontroller, or other processor or processing/controlling circuit. Similarly, the memory 128 can be any type of volatile or non-volatile memory or data storage capable of performing the functions described herein. In operation, the memory 128 may store various data and software used during operation of the user device 122, such as operating systems, applications, programs, libraries, and drivers. The memory may also access data stored locally on the scanning device 102, the user device 122, or the server 152. The memory 128 is communicatively coupled to the processor 126 such that the processor 126 can execute files located in the memory 128.

The communications circuit 132 is communicably coupled to the image circuit 130 and the display circuit 134 and is configured to send communications to, and receive communications from, the user device 122, and to send communications to, and receive communications from, the server 152. For example, the communications circuit 132 can communicate information regarding images received from the scanning device 102 to the server 152 such that the server 152 can provide the information to the monitoring system 140 and/or the aligner fabrication center 162. Additionally, the communications circuit 132 can communicate information regarding images received from the image circuit 130 to the server 152 such that the server 152 can provide the information to the monitoring system 140 and/or the aligner fabrication center 162. The communications circuit 132 can communicate with the user device 122 and the server 152 in a variety of ways including, but not limited to, Bluetooth, a WiFi network, a wired local area network (LAN), Zigbee, or any other suitable way for devices to exchange information.

The image circuit 130 is configured to save images recorded by the user device 122 in the memory 128. The image circuit 130 can access the saved images from the memory 128 to provide the images to the server 152 when the server 152 must provide the images to the monitoring system 140. The image circuit 130 is in communication with one or more cameras integrated with the user device 122, and the cameras can include one or more of a front-facing camera and a rear-facing camera.

The display circuit 134 is configured to receive information from the scanning device 102, the image circuit 130, and/or the monitoring system 140 and display the information to the user and/or provide the information to the server 152. For example, the display circuit 134 can receive information regarding the progress of the user (e.g., how close the user is to completing the treatment plan). The display circuit 134 can provide the progress information to the user by showing a visual depiction of the progress of the user on the display of the user device 122. The information can be provided in a variety of ways, as will be further described with reference to FIG. 8. As another example, the display circuit 134 can receive images of the teeth of the user from the scanning device 102 or the image circuit 130, and the display circuit 134 can display the images of the teeth of the user on the display of the user device.

The server 152 is communicably coupled to the scanning device 102, the user device 122, the monitoring system 140, and the aligner fabrication center 162. In addition to being communicably coupled to the user device 122 and the scanning device 102, the server 152 can be communicably coupled to a plurality of user devices and/or scanning devices, with each of the plurality of user devices and/or scanning devices being associated with a different user. The server 152 is configured to receive scan data from the scanning device 102 and/or image data from the user device 122 and perform additional operations based on the data in order to prepare the scan data and/or image data to send to the monitoring system 140 and/or the aligner fabrication center 162. The additional operations the server 152 can perform include, but are not limited to, high-resolution reconstruction of scanned images and converting the scanned images to one or more 3D images. The server 152 can communicate the results of the additional operations to the aligner fabrication center 162 and/or the monitoring system 140.

The monitoring system 140 is communicably coupled to the server 152 and is configured to receive two-dimensional ("2-D") image data and 3D image data and make determinations based on comparisons between image data received. The monitoring system 140 is shown to include a processing circuit 142, a communications circuit 148, and an analysis circuit 150. The processing circuit 142 is further shown to include a processor 144 and a memory 146. The processor 144 can be any type of processor capable of performing the functions described herein. The processor 144 may be a single or multi-core processor(s), digital signal processor, microcontroller, or other processor or processing/controlling circuit. Similarly, the memory 146 can be any type of volatile or non-volatile memory or data storage capable of performing the functions described herein. In operation, the memory 146 may store various data and software used during operation of the monitoring system 140, such as operating systems, applications, programs, libraries, and drivers. The memory 146 is communicatively coupled to the processor 144 such that the processor 144 can execute files located in the memory 146.

The communications circuit 148 is communicably coupled to the processing circuit 142 and the analysis circuit 150 and is configured to send communications to, and receive communications from, the server 152. For example, the communications circuit 148 can receive 2-D image data and 3D image data from the server 152, provide the data to the analysis circuit 150, receive the analysis from the analysis circuit 150, and provide the analysis to the server 152 for further dissemination.

The analysis circuit 150 is communicably coupled to the processing circuit 142 and is configured to receive images (e.g., 2-D images, 3D images, and/or scan data) from the communications circuit 148 and analyze the images (e.g., to determine differences between the images). The analysis circuit 150 can include facial recognition software such that the analysis circuit 150 is capable of recognizing the face of a user among various faces in a photograph or other image. The analysis circuit 150 can also include software (either integrated with facial recognition software or included as standalone software) that can determine specific facial features and compare facial features of a user at different times (e.g., comparing the smile of a user from today to a smile of the same user from six months ago). The analysis circuit 150 can also include software to compare images of teeth of a user to 3D models of a treatment plan for the user and determine the progress of the user relative to the treatment plan. Furthermore, the analysis circuit can include software to determine, based on photos and/or scans of teeth, the dental health of a user. For example, the dental health of a user can include elements such as tooth cleanliness, plaque buildup, gum health, presence of cavities, cracked teeth, tongue health, and other elements that can indicate the dental health of a user.

The social media system 190 is communicably coupled to the server 152 and can be any type of social media system where a user can create a profile or account and view profiles or accounts of other users over the Internet. The social media system 190 includes any interactive computer-mediated technology that facilitates the creation and sharing of information, such as photographs and videos of the user taken by the user and provided to the social media system 190 or taken by other users and provided to the social media system 190 by other users. In some embodiments, images of the user may be tagged with information identifying an identity of the user (e.g., a name or account number). A user can upload photos to the user's account such that the user and those connected to the user can view the photos. Examples of the social media system 190 include Facebook®, LinkedIn®, Instagram®, and any other systems that allow users to connect via the Internet.

The aligner fabrication center 162 is communicably coupled to the server 152 and is configured to receive the 3D images from the server 152 and generate one or more orthodontic aligners based on the 3D images. The aligner fabrication center 162 is shown to include an aligner fabrication computer system 164 and an aligner fabrication system 174. The aligner fabrication computer system 164 is configured to determine, based on the 3D images, an optimal process to reposition the teeth of the user from a first configuration to a second configuration. The aligner fabrication computer system 164 includes a communications circuit 166, an image recognition circuit 168, an image stitching circuit 170, and a 3D model creation circuit 172. The aligner fabrication system 174 is configured to create, based on one or more physical 3D models, one or more aligners operable to reposition the teeth of a user.

The communications circuit 166 is communicably coupled to the server 152 such that the server 152 provides image data to the aligner fabrication computer system 164 via the communications circuit 166. For example, the communications circuit 166 may receive 3D image data from the server 152 that is used to fabricate aligners. The communications circuit 166 can also communicate information to the server 152 for the server 152 to provide to the monitoring system 140. For example, the communications circuit 166 may provide the treatment plan to the server 152 in the form of a plurality of 3D models or images showing the position of the user's teeth in various stages of the treatment plan. The server 152 can provide the plurality of 3D models or images to the monitoring system for further analysis.

The image recognition circuit 168 is operable to receive the image data from the communications circuit 166 and determine the location of the images for further processing. For example, the image recognition circuit can receive four images of the mouth of a user, and the four images represent the scan of the entire mouth. The image recognition circuit 168 can determine which image represents the lower right quadrant of the mouth, the lower left quadrant of the mouth, the upper right quadrant of the mouth, and the upper left quadrant of the mouth such that the image recognition circuit 168 organizes the images such that the images can be stitched together.

In some embodiments, the image recognition circuit 168 can receive a different number of images of the mouth of the user. For example, in some embodiments, the image recognition circuit 168 can receive a single image of an upper dental arch of the user and a single image of the lower dental arch of the user. In some embodiments, the image recognition circuit 168 can receive multiple images (e.g., two or more images) of the upper dental arch of the user and three images of the lower dental arch of the user. Each image can represent the entirety of the user's upper or lower dental arch, or each image can represent a portion of the user's upper or lower dental arch. For example, where three images are received of the user's upper dental arch, the images can either represent the user's entire upper dental arch, or each image can represent a portion of the user's dental arch such that the three images together represent the entirety of the user's upper dental arch. Furthermore, in some embodiments, the image recognition circuit 168 can receive images of the mouth of the user 200 with the mouth of the user 200 in a closed position to receive images of a bite articulation of the user 200.

The image stitching circuit 170 receives the recognized images from the image recognition circuit 168 and stitches the images together to create images of the top and bottom teeth. In some embodiments, the image stitching circuit 170 creates one image for the top teeth and one image for the bottom teeth. In some embodiments, the image stitching circuit creates a single image that includes both the top teeth and the bottom teeth. The image stitching circuit 170 can implement any known method of stitching to stitch the images together. For example, the image stitching circuit 170 can stitch the images together using keypoint detection (e.g., finding distinct regions in images used to match images together), registration (e.g., matching features in images that minimize the sum of absolute differences between overlapping pixels), or any other known stitching method. The stitched image is provided to the 3D model creation circuit 172 for further processing.

As shown, the image stitching circuit 170 is located within the aligner fabrication center 162. However, in some embodiments, the image stitching circuit 170 may be located within the scanning device 102 such that the scanning device 102 is operable to stitch images together. In some embodiments, the image stitching circuit 170 may be located within the server 152 such that the server 152 is operable to stitch images together. Regardless of where the images are stitched together, machine learning may be used to continuously improve the image stitching process. As used herein the term "machine learning" refers to algorithms and statistical models used by a computer to perform a specific task without using explicit instructions. Machine learning algorithms that may be used in the image stitching process include, but are not limited to, supervised learning, unsupervised learning, reinforcement learning, feature learning, sparse dictionary learning, anomaly detection, and association rules. Machine learning models that may be used in the image stitching process include, but are not limited to, artificial neural networks, decision trees, support vector machines, Bayesian networks, and genetic algorithms.

The 3D model creation circuit 172 receives the stitched image and creates a 3D model from the stitched image. The 3D model creation circuit 172 can use any known method of generating a 3D model including, but not limited to, depth-based conversion, depth from motion, depth from focus, depth from perspective, or any other known method. The 3D model creation circuit 172 generates a treatment plan based on the 3D model of the teeth of the user. The treatment plan includes a first tooth configuration based on the 3D model of the teeth, and a second tooth configuration based on an optimal tooth configuration (e.g., the treatment plan can include moving the teeth from a crooked configuration to a straight configuration). The 3D model creation circuit 172 determines a number of steps in the treatment plan required to move the teeth from the first configuration to the second configuration, and generates 3D models of the teeth for each step in the treatment plan. The 3D model creation circuit 172 can also create physical representations of the 3D models via any known method including, but not limited to, 3D printing, machining, molding, or any other method capable of creating a physical 3D model. The 3D model creation circuit 172 sends the physical 3D models to the aligner fabrication system 174.

The aligner fabrication system 174 receives the physical 3D models from the 3D model creation circuit 172 and generates aligners for repositioning the teeth of a user. The aligner fabrication system 174 includes a thermoforming machine 176, a cutting machine 178, and a laser etching machine 180. The thermoforming machine 176 is operable to create an aligner by placing a sheet of polymeric material on top of one or more 3D models. The polymeric material is heating and drawn tightly over the 3D models (e.g., via a vacuum system, a press, or any other known methods). The polymeric material is allowed to cool, and the thermoformed polymeric material is removed from the 3D model.

The cutting machine 178 receives the thermoformed polymeric material from the thermoforming machine 176 and is operable to trim excess polymeric material from the thermoformed polymeric material. The excess material is trimmed with a cutting system (e.g., using lasers, mechanical methods, or other known cutting methods) to generate the aligners.

The laser etching machine 180 is operable to include identification marks on the aligners via a laser etching process. The identification marks can include a user specific number, a sequence number indicating how the aligner should be worn in sequence with other aligners, or any other type of marks that can provide an identifying feature.

As described, the images recorded by the scanning device 102 and/or the user device 122 can be processed and modified by the scanning device 102, the user device 122, the server 152, and/or the aligner fabrication center 162. In some embodiments, the images recorded by the scanning device 102 can be at least partially processed by a combination of at least two or more of the scanning device 102, the user device 122, the server 152, or the aligner fabrication center 162 such that the combination of partial processing results in fully processed and modified images.

Figure 2:
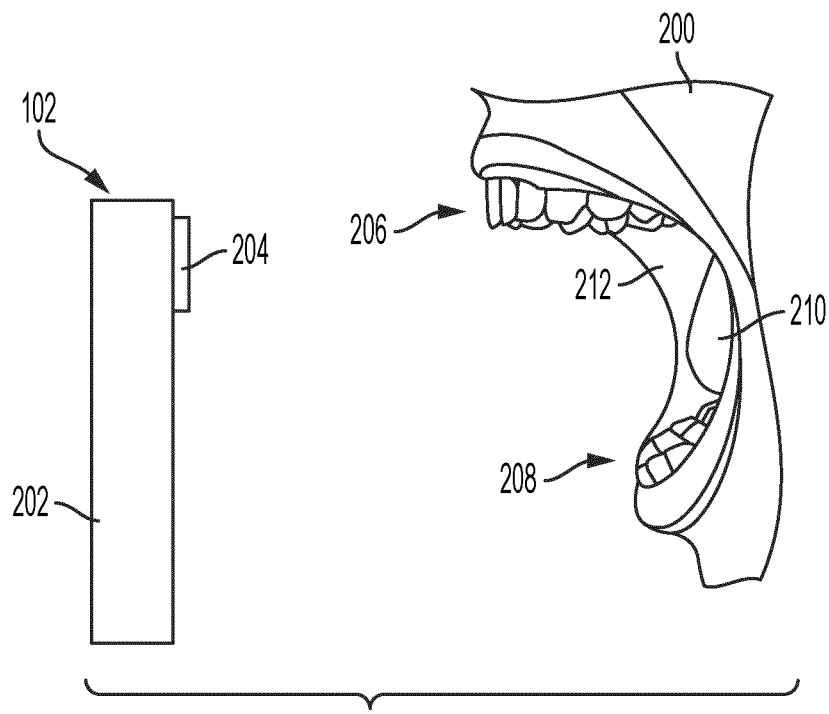
FIG. 2 is an illustration of a user scanning a mouth, according to some embodiments.

Referring now to FIG. 2, an illustration of a user 200 scanning a mouth with the scanning device 102 is shown, according to some embodiments. The scanning device 102 can be any known device capable of capturing images of a 3D object for creating a 3D model. The scanning device 102 includes a body 202 and a camera 204. The body 202 is sized and configured to be held in the hand of the user 200 during a scan of the teeth of the user 200. In another embodiment, a person other than the user 200 having their teeth being scanned can hold and operate the scanning device 102 to scan the teeth of the user 200. The body 202 can be manufactured from a plastic material (e.g., polycarbonate, polyethylene, or any other suitable plastic), a metal material (e.g., aluminum, stainless steel, or any other suitable metal), or any other material suitable for the application.

The camera 204 is coupled to the body 202 and can be any type of system or device configured to capture 2-D or 3D images (e.g., a dedicated oral scanner, a smartphone, a tablet computer, a digital camera). In some embodiments, the camera 204 includes a plurality of cameras arranged on the body 202 to provide for a variety of perspectives of the target image.

The user 200 includes upper teeth 206, lower teeth 208, a tongue 210, and an oral cavity 212 (e.g., the inside of the cheek, the gums, and other soft tissues inside the mouth). In some embodiments, the user 200 can scan the upper teeth 206, the lower teeth 208, the tongue 210, and the oral cavity 212 simultaneously with the scanning device 102. In some embodiments, the user 200 can scan the upper teeth 206, the lower teeth 208, the tongue 210, and the oral cavity 212 in separate scans.

In some arrangements, the scanning device 102 is not used to scan the mouth of the user 200. In such arrangements, the user device 122 can be used to scan the mouth of the user in a manner substantially similar to scanning the mouth using the scanning device 102.

Regardless of whether the mouth is scanned with the scanning device 102 or the user device 122, after the scan is complete the images recorded during the scan can be transmitted to the monitoring system 140 via the server 152 for further processing and/or analysis.

Figure 3:
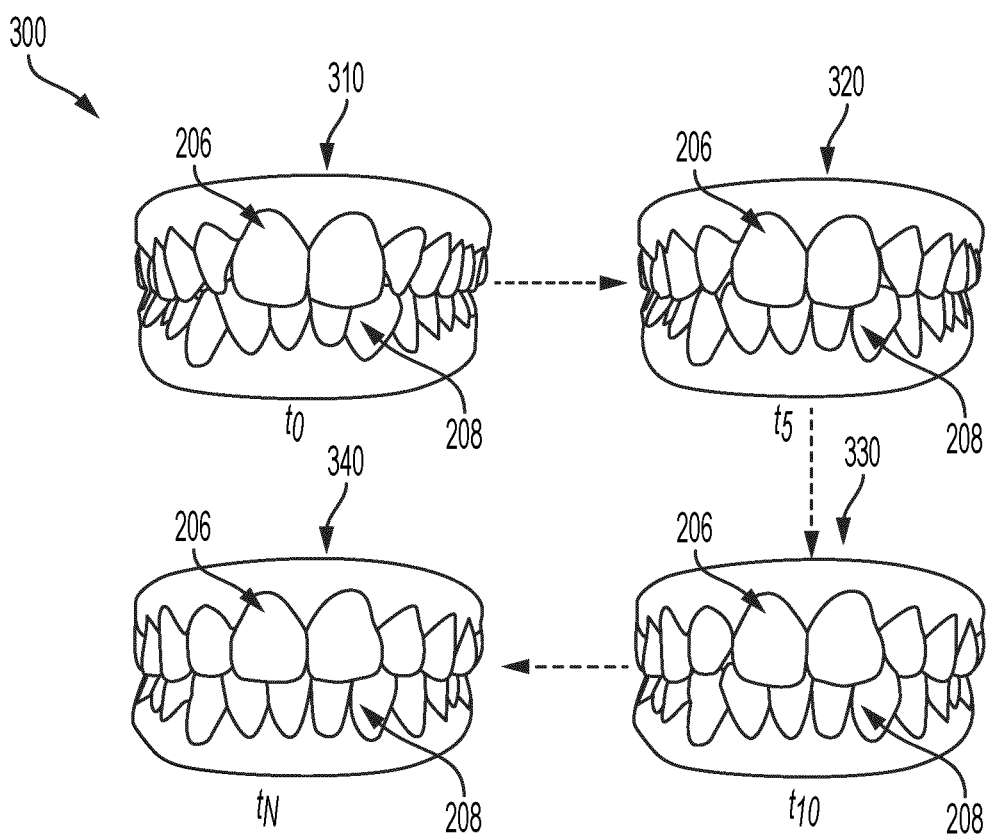
FIG. 3 is an illustration of stages of an orthodontic treatment plan, according to some embodiments.

Referring now to FIG. 3, an illustration of stages of an orthodontic treatment plan 300 is shown, according to some embodiments. The treatment plan 300 is shown to include a first 3D model 310, a second 3D model 320, a third 3D model 330, and a final 3D model 340 (collectively referred to herein as "3D models 310-340"). The 3D models 310-340 can be generated by the 3D model creation circuit 172 and be based on an initial scan provided to the 3D model creation circuit 172 by the scanning device 102 or the user device 122.

The first 3D model 310 represents an initial configuration of the upper teeth 206 and the lower teeth 208 at a time $t_0$. For example, the first 3D model 310 can represent the configuration of the upper teeth 206 and the lower teeth 208 prior to an orthodontic treatment (e.g., treatment with one or more aligners). The final 3D model 340 represents a final configuration of the upper teeth 206 and the lower teeth 208 at a time $t_N$. For example, the final 3D model 340 can represent the configuration of the upper teeth 206 and the lower teeth 208 after the orthodontic treatment is complete (e.g., eighteen months after beginning the orthodontic treatment). The second 3D model 320 and the third 3D model 330 represent interim configurations (at times $t_5$ and $t_{10}$, respectively) of the upper teeth 206 and the lower teeth 208 during the orthodontic treatment. For example, $t_5$ can represent a time five months after beginning the orthodontic treatment, and $t_{10}$ can represent a time ten months after beginning the orthodontic treatment.

As one of ordinary skill would understand, the number of 3D models generated is based on the configuration of the teeth of the user 200 prior to the orthodontic treatment. Accordingly, the number of 3D models generated can be greater than or less than the number depicted in FIG. 3. For example, a first user may have teeth with an initial configuration that may require 36 months of treatment, and a second user may have teeth with an initial configuration that may require only 6 months of treatment.

In some embodiments, the user 200 may elect to move his/her teeth from an initial configuration to a final configuration using dental aligners. After scanning the upper teeth 206 and the lower teeth 208, the treatment plan 300 is determined by the aligner fabrication center 162, as described. For example, the user 200 may require eighteen months of treatment, with the user 200 being provided with four aligners per month. Accordingly, the treatment plan 300 may include seventy-two different 3D models if one aligner is manufactured from each model, twenty-four different 3D models if three aligners are manufactured from each model, or other number of 3D models based on the number of aligners manufactured from each model.

Figure 4:
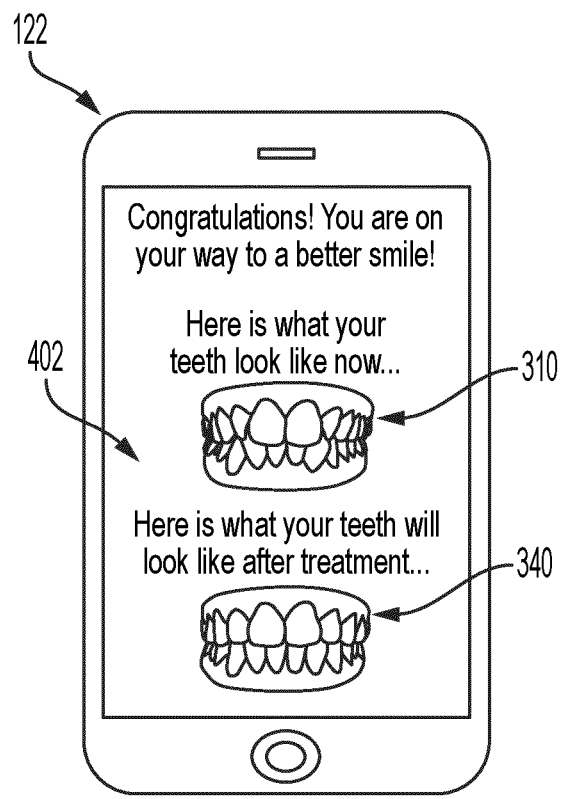
FIG. 4 is an illustration of a mobile device application displaying a treatment plan to a user, according to some embodiments.

Referring to FIG. 4, an illustration of a mobile device application displaying the treatment plan to a user is shown, according to some embodiments. In some embodiments, when the user 200 begins treatment with dental aligners, the user 200 is provided with access to a mobile application that provides the user with the ability to monitor the progress of the treatment. Access to the mobile application can be provided by the manufacturer of the aligners, and the manufacturer can provide the user 200 with an initial user name and password to use in order to access the specific treatment plan of the user 200. The user 200 can download the application to the user device 122 for access.

When the user 200 logs in to the application for the first time, a message is displayed on a display 402 of the user device 122 along with depictions of the first 3D model 310 and the final 3D model 340. The depictions allow the user 200 to compare what the teeth of the user 200 will look like when the treatment is complete to what the teeth of the user 200 look like before treatment. In some embodiments, additional 3D models (e.g., intermediate 3D models indicating the position of the teeth at intermediate points during treatment) may be displayed to the user 200 to allow the user 200 to view the teeth at various times during treatment.

Figure 5:
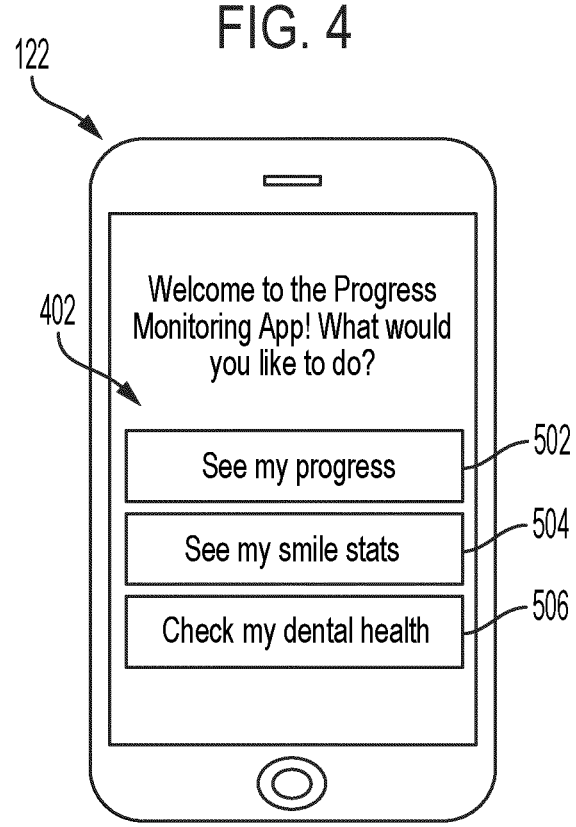
FIG. 5 is an illustration of a mobile device application providing viewing options to a user, according to some embodiments.

Referring to FIG. 5, an illustration of the mobile device application providing viewing options to the user 200 is shown, according to some embodiments. The display 402 includes a progress button 502, a smile button 504, and a dental health button 506. After welcome screen is displayed to the user 200 as shown in FIG. 4, the mobile application may prompt the user 200 to choose an action by selecting one of the progress button 502, the smile button 504, and the dental health button 506.

Figure 6:
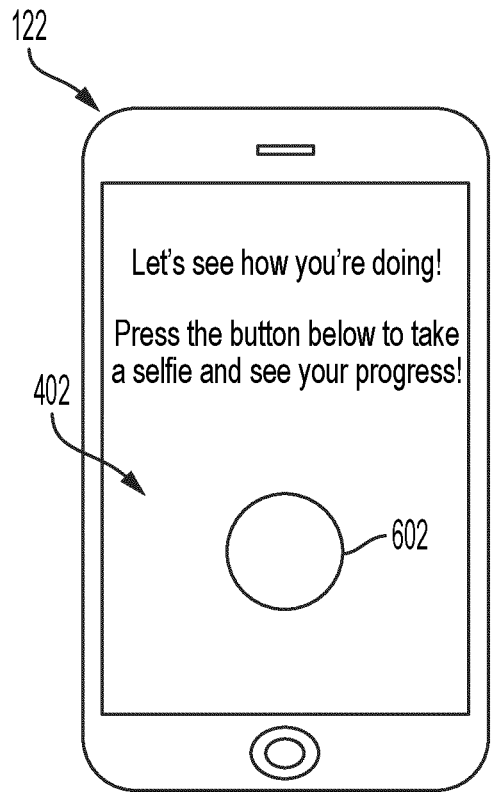
FIGS. 6-8 are illustrations of a mobile device application providing feedback to a user regarding the user's progress, according to some embodiments.
Figure 7:
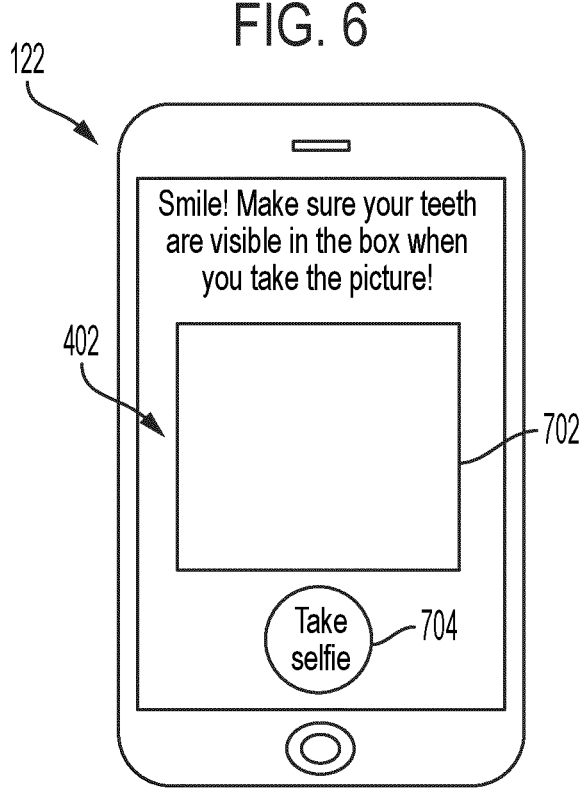
Figure 8:
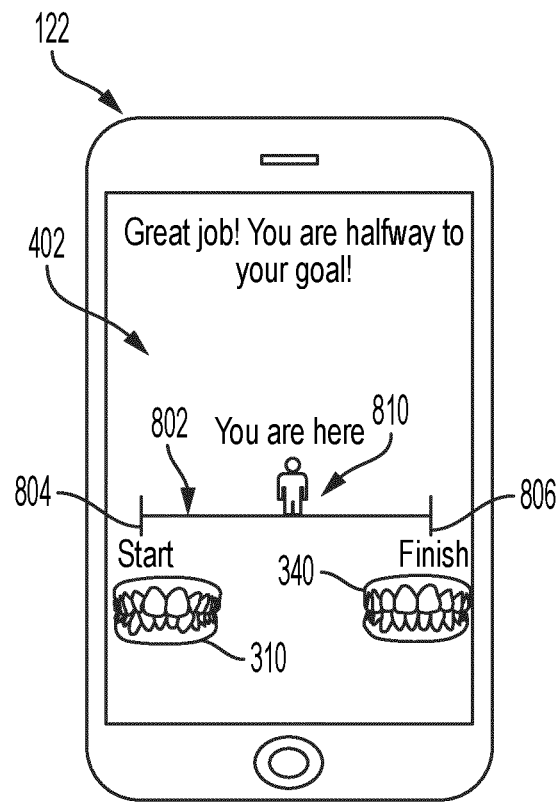

Referring to FIGS. 6-8, illustrations of the mobile device application providing feedback to the user 200 regarding the user's progress is shown, according to some embodiments. When provided with the options in FIG. 5, the user 200 may desire to view the progress of the treatment, and the user 200 selects the progress button 502 to view the progress. As shown in FIG. 6, the mobile application prompts the user to take a selfie photograph such that an accurate progress can be calculated. As referred to herein, a "selfie" is a photo taken of oneself using the front-facing camera of a device equipped with such a camera. For example, the user device 122 may be a mobile device such as a mobile phone, and the mobile phone may include a front-facing camera. The mobile application presents the user 200 with a button 602 on the display 402 and prompts the user 200 to press the button 602 to take a selfie to measure the progress of the user 200. In some embodiments, a photograph of the user 200 is taken by another person using the user device 122 or using another device and then providing the photograph to the user 200 via the user device 122.

As shown in FIG. 7, the mobile application then prompts the user to take a selfie by providing a box 702 in which the teeth of the user 200 should be positioned to take the selfie. In some embodiments, the user 200 smiles such that the teeth of the user 200 are positioned in the box 702. In some embodiments, the user 200 configures the mouth of the user 200 such that the user displays as many teeth as possible in the box 702 (e.g., the user 200 does not smile, but spreads his/her lips as far as possible). The user 200 then takes the selfie by pressing a selfie button 704 provided on the display 402. The selfie taken by the user 200 is provided to the monitoring system 140 for further analysis. The mobile application communicates with the monitoring system 140 via the server 152 to provide the user 200 with feedback regarding a progress of a treatment plan of the user 200 or information regarding an oral health condition.

In some embodiments, the user 200 can conduct another scan of the teeth instead of taking a selfie. In such embodiments, the mobile application can prompt the user to conduct another scan of the teeth using the scanning device 102. After successfully conducting the scan of the teeth, the scanning device 102 provides the scan data to the monitoring system 140 for further analysis. The user 200 notifies the mobile application that the scan is complete, and the mobile application communicates with the monitoring system 140 via the server 152 to provide the user 200 with feedback regarding a progress of a treatment plan of the user 200 or information regarding an oral health condition.

As shown in FIG. 8, after analyzing the selfie and/or scan by the user 200 (the analysis of the selfie and/or scan will be further described with reference to FIG. 12), the user 200 is provided with the treatment progress or the information regarding an oral health condition on the display 402. In some embodiments, the display 402 includes a treatment timeline 802. The treatment timeline 802 includes a treatment start 804, a treatment finish 806, and a current position 810. The treatment start 804 indicates the beginning of the treatment plan and is represented by a line crossing the treatment timeline 802. The treatment start 804 may also include an image of the first 3D model 310 to remind the user 200 of the state of the teeth of the user 200 when treatment began. The treatment finish 806 indicates the end of the treatment plan and is represented by a line crossing the treatment timeline 802. The treatment finish 806 may also include an image of the final 3D model 340 to remind the user 200 of how the teeth of the user 200 will look when treatment is complete. The current position 810 represents how close the user 200 is to completing treatment. The current position 810 can be represented in a variety of ways. As shown in FIG. 8, the current position 810 is represented by a generic icon. In some embodiments, the current position 810 can be represented by an image of the most recent selfie or scan taken by the user such that the user can see how the current configuration of the teeth of the user 200 compares to the final 3D model 340.

The progress of the user 200 can be represented in a variety of other ways on the display 402. For example, the progress of the user 200 can be shown as a pie chart, with an empty pie chart indicating the user 200 has not started treatment and a full pie chart indicating the user 200 has completed treatment. As another example, the progress of the user 200 can be shown as a number indicating the percent completion of the treatment plan, with 0% indicating the user 200 has not started treatment and 100% indicating the user 200 has completed treatment. As an additional example, the progress of the user 200 can be shown as a gauge similar to a fuel gauge in a vehicle, where an "empty" gauge indicates the user has not started treatment and a "full" gauge indicates the user has completed treatment.

Figure 9:
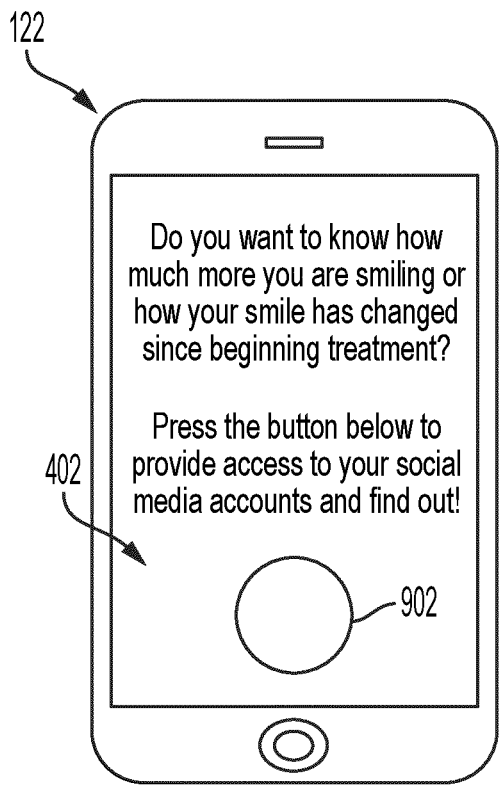
FIGS. 9-10 are illustrations of a mobile device application providing feedback to a user regarding the user's smile, according to some embodiments.
Figure 10:
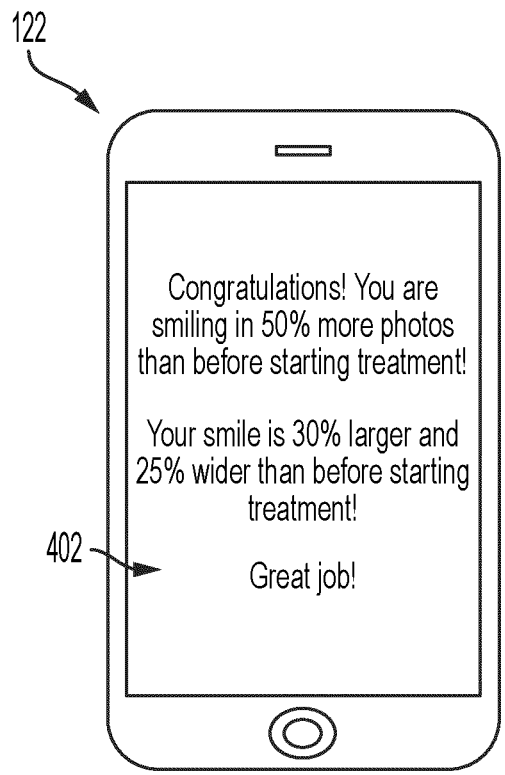

Referring now to FIGS. 9-10, illustrations of a mobile device application providing feedback to the user 200 regarding the user's smile are shown, according to some embodiments. In some embodiments, the mobile application may request access to the social media accounts of the user 200 on the social media system 190 in order to view the images of the user 200 posted to his/her social media accounts or to social media accounts of others. The mobile application can provide those images to the user device 122, and the user device 122 can provide the images to the monitoring system 140 via the server 152 for further analysis. Analysis of the images by the monitoring system 140 will be further described with reference to FIG. 12.

With reference to FIG. 5, the user 200 may select the smile button 504 to view statistics associated with the smile of the user 200. After pressing the smile button 504, the user may be presented with the message on the display 402 as shown in FIG. 9, with a prompt for the user to press a button 902 to view smile statistics. In some embodiments, access to the social media accounts of the user 200 is granted by pressing the button 902. For example, each time the user presses the button 902, access is granted to the social media accounts of the user 200 for a specified period (e.g., two minutes) such that the mobile application can download images posted to the social media accounts of the user 200 since the last time the user granted access to the social media accounts. After downloading the images, the mobile application provides the images to the monitoring system 140 via the server 152 for further analysis.

In some embodiments, access to the social media accounts of the user 200 is continuous such that the mobile application downloads images posted to the social media accounts of the user 200, or posted to other social media accounts but tagging the user, as the images are uploaded to the social media accounts, and provides those images to the monitoring system 140 via the server 152. In such embodiments, pressing the button 902 to view smile statistics directs the monitoring system 140 to begin the analysis of the images.

After performing the analysis, the monitoring system 140 provides the analysis to the mobile application via the server 152 such that the mobile application can show the user 200 his/her smile statistics on the display 402. As shown in FIG. 10, the display 402 may provide the user with information associated with the smile of the user 200. For example, the display 402 may provide the user with information regarding a comparison of the number of photos in which the user 200 is smiling in photos prior to treatment and the number of photos in which the user 200 is currently smiling based on the most recent photos on the social media accounts of the user 200 (e.g., the user 200 may be smiling in 50% more photos now than before starting treatment).

In addition, the display 402 may provide statistics regarding the attributes of the smile of the user 200. The attributes of the smile may include items such as the height of the smile (e.g., the distance between the top and bottom lips when smiling), the width of the smile (e.g., the distance between the corners of the lips when smiling), the number of teeth visible when smiling, and any other measurable attributes of a smile. For example, the display 402 may provide the user with information regarding how much larger and wider the smile of the user 200 is based on current social media photos than the width and length of the smile of the user 200 at the start of treatment.

Figure 11:
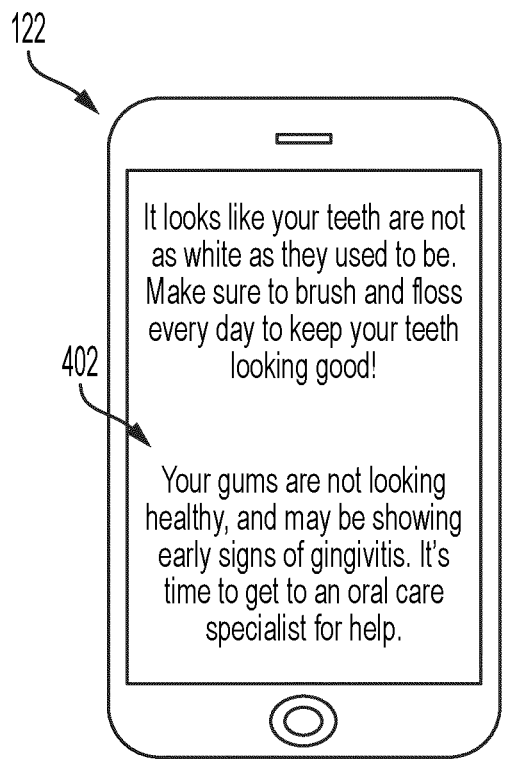
FIG. 11 is an illustration of a mobile device application providing feedback to a user regarding the user's dental condition, according to some embodiments.

Referring to FIG. 11, an illustration of a mobile device application providing feedback to a user 200 regarding the user's dental condition is shown, according to some embodiments. With reference to FIG. 5, the user 200 may select the dental health button 506 to view feedback regarding the dental health of the user 200. After pressing the dental health button 506, the user may be presented with a message on the display 402 that indicates the dental health of the user 200. In some embodiments, the display 402 can provide information to the user 200 regarding the condition of the teeth of the user (e.g., the whiteness of the teeth, the amount of plaque on the teeth, whether the teeth have cavities or are cracked, and other conditions related to the teeth), the condition of the gums of the user (e.g., whether the gums exhibit signs of gingivitis, are swollen, and other conditions related to the gums), and the condition of the oral cavity of the user (e.g., the presence of canker sores, bacterial buildup, and other conditions related to the oral cavity).

Figure 12:
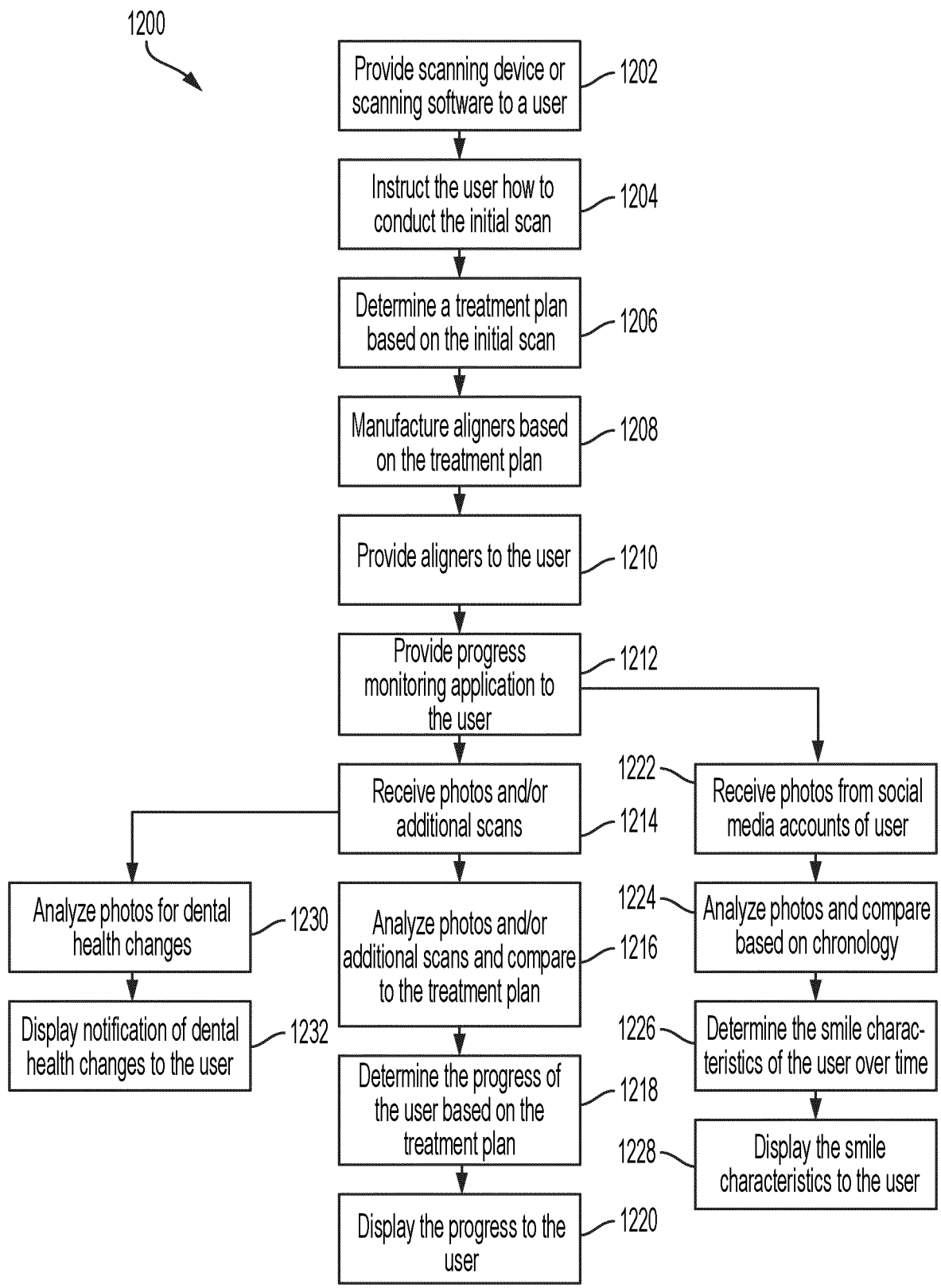
FIG. 12 is a flow diagram of a method for monitoring the progress and dental condition of a user, according to some embodiments.

Referring now to FIG. 12, a flow diagram of a method 1200 for monitoring the progress and dental condition of the user 200 is shown, according to some embodiments. At 1202, a scanner or scanning software is provided to the user 200. For example, the user 200 is provided with the scanning device 102 by the manufacturer of the scanning device 102 or the aligner manufacturer. The user 200 may also be provided with scanning software to be used with the user device 122. For example, the user 200 may be provided with a software download for the user device 122 that includes the scanning software such that the user 200 can use the user device 122 to conduct a scan of the teeth of the user 200. Additionally, the scanning device 102 may be paired with the user device 122 (e.g., via a Bluetooth connection) such that the scanning device 102 is in communication with the user device 122. Scan data generated by the scanning device 102 can then be shared with the user device 122.

At 1204, the user 200 is instructed how to conduct an initial scan of the teeth of the user 200. For example, the scanning device 102 may include instructions the user 200 can follow to conduct an acceptable scan of the teeth of the user 200. The instructions may include elements such as the appropriate distance at which to maintain the scanning device 102 from the teeth of the user 200 during the scan, the speed at which the user 200 should move the scanning device 102 during the scan, how to orient the scanning device 102, whether more than one scan is required, and other aspects related to scanning the teeth of the user 200 with the scanning device 102. As another example, the scanning device 102 may be paired with the user device 122, and the user may be provided with a software application associated with the scanning device 102 that can be executed on the user device 122. The software application can provide instructions to the user 200 regarding conducting an acceptable scan with the scanning device 102. In some embodiments, the instructions can include text on the display 402 of the user device 122. In some embodiments, the instructions can include graphics on the display 402 of the user device 122. The instructions may also include real-time tracking of the scanning device 102 during a scan such that real-time feedback is provided to the user 200 during the scan regarding the acceptability of the scan. As an additional example, the user device 122 can be used to conduct the scan of the teeth of the user 200 using software provided at 1202. The software can include instructions regarding how to conduct an acceptable scan as described. After the initial scan is conducted, the data from the initial scan is provided to the aligner fabrication center 162 and the monitoring system 140 via the server 152.

At 1206, a treatment plan is determined based on the initial scan. For example, the communications circuit 166 can receive the initial scan data and provide the data to the image recognition circuit 168 such that the image recognition circuit identifies teeth and/or other oral landmarks from the initial scan. The image stitching circuit 170 stitches one or more scans together based on the identified teeth and/or other oral landmarks to create an image of the teeth of the user 200. In some embodiments, the image can include one image that incorporates both the top teeth and the bottom teeth of the user 200. In some embodiments, the image can include one image of the top teeth and one image of the bottom teeth of the user 200. The image is provided to the 3D model creation circuit 172, which determines the final configuration of the teeth of the user 200 based on the initial scan data. For example, the 3D model creation circuit 172 may determine that, to move the teeth from the initial configuration to the final configuration requires twenty-four different sets of aligners (e.g., the treatment plan). The 3D model creation circuit 172 creates a 3D model corresponding to each of the twenty-four sets of aligners required. The 3D models can include both computer models and physical models (e.g., models created by a 3D printer, or machined from a block of material). The computer and/or physical 3D models created by the 3D model creation circuit 172 are then provided to the aligner fabrication system 174 and the monitoring system 140. The computer 3D models can be stored in the memory 146 of the monitoring system 140 for future use.

At 1208, aligners are manufactured based on the treatment plan. For example, the aligner fabrication system 174 receives the physical 3D models of the treatment plan from the aligner fabrication computer system 164. The 3D models are used in the thermoforming machine 176 to create the aligners to be provided to the user 200. Any additional material on the aligners is removed using the cutting machine 178, and the aligners may be etched with identifying markings (e.g., a number corresponding to the order in which the aligners should be worn) by the laser etching machine 180. In some embodiments, the aligners are manufactured by a 3D printer after sending the computer 3D models to the 3D printer, thereby bypassing the thermoforming and cutting processes.

At 1210, the aligners are provided to the user 200. For example, the user 200 receives the full set of aligners (e.g., all twenty-four aligners) with instructions regarding when to use each set of aligners. The user 200 may also receive the aligners in batches (e.g., each batch can include eight sets of aligners) such that the user 200 does not receive the second batch of aligners until the user 200 has worn the first six sets of aligners in the first batch, in an example embodiment.

At 1212, the user 200 is provided with a progress monitoring application. For example, the manufacturer of the dental aligners provides the user 200 with a link to download an application on the user device 122 that communicates with the monitoring system 140. In some embodiments, the monitoring system is part of the application, and after downloading the application, the monitoring system 140 is located on the user device 122.

At 1214, photos and/or additional scans are received. For example, to open the progress monitoring application, the user 200 may be required to provide a selfie image, which can then be used by the analysis circuit 150 as part of any process or system described herein that uses images of the user. In some embodiments, the user must smile to open the progress monitoring application and only once the progress monitoring application determines that the user has smiled wide enough (e.g., or shown a threshold number of teeth and threshold amount), will the progress monitoring application open. In some embodiments, the progress monitoring application prompts the user to smile to open the application. Upon opening the progress monitoring application on the user device 122, the progress monitoring application may prompt the user to take a selfie by locating the mouth of the user in the box 702 and pressing the selfie button 704. In some embodiments, the user 200 may be required to smile when taking the selfie. In some embodiments, the user 200 may be required to stretch the lips of the user such that substantially all of the top and bottom teeth of the user 200 are visible in the box 702. The lips of the user 200 may be stretched using the facial muscles of the user 200, in some embodiments. The lips of the user 200 may also be stretched using a device configured to stretch the lips. The upper teeth 206 and the lower teeth 208 of the user 200 can be touching during the selfie, in some arrangements. The upper teeth 206 and the lower teeth 208 of the user 200 may also be separated in some arrangements such that various surfaces of the upper teeth 206 and the lower teeth 208 (e.g., the buccal surface, the lingual surface, the labial surface, the occlusal surface, the mesial surface, and the distal surface) are captured during the selfie.

In another example embodiment, the user 200 may be prompted to conduct an additional scan of the teeth using the scanning device 102 before taking further actions within the progress monitoring application. The user 200 can conduct the scan in the same manner as described associated with the initial scan, and the scan data is provided to the monitoring system 140.

The selfie and/or scan is stored in the memory 146. Each selfie and/or scan may be tagged by the monitoring system 140 such that each selfie and/or scan includes the date and time at which the selfie and/or scan was added to the memory 146.

At 1216, the photos and/or additional scans are analyzed and compared to the treatment plan. For example, the user 200 may desire to view the progress made toward the final configuration, and the user selects the progress button 502. Upon selecting the progress button 502, the analysis circuit 150 determines the appropriate 3D model to use as an initial comparison for the analysis. For example, the user 200 may be scheduled to be wearing the tenth aligner in the set of twenty-four aligners based on the treatment plan; therefore, the analysis circuit determines that the appropriate 3D model to use for an initial comparison is the 3D model corresponding to the tenth aligner.

The analysis circuit 150 receives the most recent photo and/or scan of the teeth of the user 200 from the memory 146 and determines the position of the teeth. For example, the analysis circuit 150 may determine the position of the teeth by determining the location of each tooth relative to all other teeth. The location can include the distance between teeth, orientation of teeth relative to each other, and other properties that may be useful in determining the position of the teeth. In some embodiments, the position is determined by identifying one or more points on a tooth (e.g., landmarks) and calculating the location of those points relative to points on all other teeth.

The analysis circuit 150 then compares the locations calculated based on the most recent photo and/or scan to the corresponding locations on the appropriate 3D model. For example, if the user 200 is scheduled to be wearing the tenth aligner, the analysis circuit will compare the locations calculated based on the most recent photo and/or scan to the locations on the tenth 3D model to determine the difference between the measured locations and the 3D model locations. The analysis circuit 150 then compares the locations calculated based on the most recent photo and/or scan to other 3D models. For example, the analysis circuit 150 compares the locations calculated based on the most recent photo and/or scan to the ninth and eleventh 3D models to determine the difference between the measured locations and the 3D model locations.

At 1218, the progress of the user is determined based on the treatment plan. For example, the analysis circuit 150 may determine that the difference between the measured locations and the locations on the 3D are the smallest when comparing the locations calculated based on the most recent photo and/or scan to the eleventh 3D model. Such a determination would indicate that the position of the teeth of the user 200 correspond most closely to the position of the teeth in the eleventh 3D model (or, for example, the computer model that represents the aligner shape for the eleventh aligner) according to the treatment plan. Continuing with the example of twenty-four aligners (e.g., twenty-four 3D models), the analysis circuit 150 determines that the user has completed approximately 46% (e.g., 11/24) of the treatment.

At 1220, the progress is displayed to the user. For example, the progress is displayed to the user on the display 402 of the user device 122. The progress can be displayed as a percentage of completion, a pie chart, or any other way to visualize the progress of the user 200 toward the completion of the treatment, as described.

In some embodiments, the monitoring system 140 can provide feedback to the user 200 regarding the progress via the display 402. In embodiments where the user 200 is on track, the monitoring system 140 may provide encouragement to the user to continue treatment as planned.

The monitoring system 140 may also provide a way for the user to consider the treatment plan as a game to maintain or increase compliance with the treatment plan. For example, the monitoring system 140 may issue points to the user based on the compliance level of the user, where more points are issued for greater compliance. In some embodiments, the user's progress can be tracked and displayed to the user in comparison to other users (e.g., an average user, by other similarly situated users, by geographic location such as country, state, city, or zip code). In some embodiments, the user may be awarded icons or "badges" for completing certain milestones in treatment (e.g., for a tooth being moved a threshold distance, for completing a certain percentage of the treatment plan, for wearing aligners as recommended for a threshold period of time or a threshold number of days, weeks, or months). In embodiments where the user 200 is behind schedule, the monitoring system 140 may provide recommendations to wear the aligners for a longer period to get back on track. For example, the monitoring system 140 may recommend that the user 200 change the aligner currently being worn to a different aligner. The monitoring system 140 may recommend that the user change the amount of time a particular aligner should be worn (e.g., the current aligner should be worn for an additional week, the current aligner should be worn for two fewer days than prescribed by the original treatment plan). The monitoring system 140 may also alert the user that a mid-course correction is needed. If a mid-course correction is needed, the monitoring system 140 may provide the user 200 with an order form to order an impression kit or provide the user with an option to schedule an appointment at a scanning center where a scan of the user's mouth can be taken. In another embodiment, if a mid-course correction is needed, the monitoring system 140 may direct the user 200 to conduct another scan of the mouth with the scanning device 102 such that additional aligners can be created based on the current configuration of the teeth of the user 200. In some embodiments, the monitoring system 140 may use data from available photos (e.g., selfie photos taken for monitoring purposes, or photos from the social media system 190) to determine the current configuration of the teeth such that additional aligners can be created without an additional scan. In some embodiments, the monitoring system 140 may be able to determine a first portion of the current configuration of the teeth of the user, and the scanning device 102 may be used to determine a second portion of the current configuration of the teeth of the user such that the combination of the first portion and the second portion provide the current configuration of the teeth of the user such that additional aligners can be created.

In some arrangements, the monitoring system 140 may determine that additional information regarding the fit of the aligner on the teeth of the user 200 is required. For example, if the user 200 is behind schedule, the monitoring system 140 may request (via the display 402) that the user take another photo and/or scan of the teeth with the aligners on the teeth. The analysis circuit 150 then analyzes the photo and/or scan of the teeth with the aligners and determines whether the aligners fit properly. For example, the analysis circuit 150 may determine that the aligners do not sit properly on the teeth and are therefore not providing the appropriate force to the teeth to provide the desired movement. The analysis circuit may determine that the user 200 should revert to a previous set of aligners for a certain period of time in order to get back on track or direct the user to use an auxiliary product to seat the aligner on their teeth (e.g., an object that the user can bite down onto to press the aligners over their teeth more tightly). For example, the user 200 may currently be wearing the tenth set of aligners, but the analysis circuit determines that the tenth set of aligners does not fit properly. The analysis circuit 150 may further determine that the position of the teeth of the user 200 more closely resembles the position of the teeth associated with the eighth 3D model. The monitoring system 140 may provide feedback to the user 200 via the display 402 that the user 200 should revert to the eighth set of aligners to get back on track. In another example, the analysis system 150 may determine that a mid-course correction is required, and the monitoring system 140 may provide the user 200 with information regarding how to implement the mid-course correction (e.g., by ordering a dental impression kit, scheduling an appointment to scan their mouth, conducting a scan of their mouth). The analysis system 150 may also determine that the user 200 may need to wear a certain aligner for a longer time to get back on track, and the monitoring system 140 may provide the feedback to the user 200. In another embodiment, the analysis system 150 may provide the user 200 with alternatives to induce a better fit with the current aligner. For example, the analysis system 150 may notify the user 200 that the current aligner would fit better if the user 200 kept the upper and lower teeth together (e.g., in a biting position) to force the aligner into position and force the teeth to move according to the aligner.

In some embodiments, the analysis circuit 150 may determine additional information regarding the aligner. For example, if the user 200 provides an additional photo and/or scan while wearing the aligners, the analysis circuit 150 may determine that the aligner is damaged or otherwise ineffective. The shape of the aligner may be distorted (e.g., the shape of the aligner is different from the manufactured shape), the aligner may exhibit abrasions, or the aligner may be fractured. If the analysis circuit 150 determines that the aligner is damaged, the monitoring system may advise the user 200 via the display 402 that the user 200 should revert to the previous aligner and a new, undamaged aligner will be manufactured and sent to the user 200.

At 1230, the photos and/or scans are analyzed to determine the dental health of the user 200. For example, the analysis circuit 150 may have the ability to differentiate colors and/or shades of colors of the teeth and/or other structures located in the oral cavity of the user 200. The analysis circuit 150 may compare the colors of some teeth of the user 200 to other teeth of the user 200 to determine whether some of the teeth of the user 200 are discolored. The analysis circuit 150 may also compare the colors of the teeth of the user 200 to a color standard stored in the memory 146 to determine whether some of the teeth of the user 200 are discolored. If a determination is made by the analysis circuit 150 that the teeth of the user are discolored, the monitoring system 140 may provide feedback via the display 402 regarding the determination at 1232.

As another example, the analysis circuit 150 may provide additional analysis regarding the health of the teeth of user. The analysis circuit 150 may have the ability to determine the level of plaque on the teeth of the user 200. If the level of plaque on the teeth of the user 200 is determined to be excessive or above a certain threshold (e.g., the plaque layer is greater than approximately 0.5 millimeters thick), the analysis circuit 150 may determine that the user 200 should be notified. The monitoring system 140 then notifies the user 200 of the excessive plaque via the display 402. The analysis circuit 150 may also have the ability to determine whether the teeth of the user 200 are damaged. Damage to a tooth can include cavities, abrasions, fractures, spots, and debonding of a dental restoration (e.g., a crown or dental implant). The analysis circuit 150 may determine whether the teeth are damaged by comparing the image of the teeth in the most recent photo and/or scan provided by the user 200 to previous photos and/or scans and/or the 3D models and/or photos from the social media system 190. The comparison may indicate the appearance of a dark spot on a tooth that was not previously there (e.g., a cavity, an abrasion, or debonding), or a deep fissure in a tooth that was not visible on previous photos and/or scans (e.g., a fracture or debonding).

In some embodiments, the analysis circuit 150 may provide additional analysis regarding the health of the tongue of the user 200. The analysis circuit 150 may have the ability to determine the color of the tongue (or various colors of the tongue if the tongue exhibits different colors in different locations) and compare the color(s) of the tongue to various color standards that may be stored in the memory 146. For example, if the tongue has a white coating or white spots, it may be an indication that the user 200 has oral thrush, leukoplakia, or oral lichen planus. If the tongue is red, it may be an indication that the user has scarlet fever or Kawasaki disease. A tongue with large bumps on it may indicate that the user 200 suffers from canker sores or may have mouth cancer. If the analysis circuit 150 determines that the tongue of the user 200 indicates a problem, the monitoring system 140 can alert the user 200 of the issue via the display 402 at 1232.

In another example, the analysis circuit 150 may provide additional analysis regarding the health of the gums (e.g., gingiva) of the user 200. For example, the analysis circuit 150 may have the ability to determine whether the gums are receding or whether the user 200 has gingivitis. The analysis circuit 150 may be able to make such determinations by identifying dark spaces in between the teeth of the user 200. If the analysis circuit 150 determines that the user 200 may have receding gums or gingivitis, the monitoring system 140 can alert the user 200 of the issue via the display 402 at 1232.

The analysis circuit 150 may also provide additional analysis regarding tooth eruption. By comparing the most recent photos and/or scans to previous photos and/or scans stored in the memory 146, the analysis circuit 150 can determine whether the user 200 exhibits any issues with tooth eruption. For example, the analysis circuit 150 can determine whether there are any submerged teeth that have not yet erupted, whether one or more teeth have erupted ectopically (e.g., in the wrong place), when a tooth erupts in the crossbite of the user 200, or when a tooth erupts exhibiting a severe rotation. If the analysis circuit 150 determines that one or more teeth of the user 200 exhibits any of these issues, the monitoring system 140 can alert the user 200 of the issue via the display 402 at 1232. Furthermore, the analysis regarding tooth eruption may determine whether the user is a candidate for treatment. For example, a fully erupted set of teeth may be required to begin treatment. If, during the initial scan, a fully erupted set of permanent teeth is not detected, the user can be notified. The monitoring system 140 may then monitor images of the user to determine when a fully erupted set of teeth is present, and notify the user that the user is ready for treatment.

In another example, the analysis circuit 150 may provide additional analysis regarding the health of the oral mucosa (e.g., the mucous membrane lining the inside of the mouth). For example, the analysis circuit 150 may be configured to determine whether the oral mucosa includes sores, blisters, or ulcers by detecting changes in color or depth in the oral mucosa. If the analysis circuit 150 determines that the oral mucosa of the user 200 exhibits signs of sores or blisters, the monitoring system 140 can alert the user 200 of the issue via the display 402 at 1232.

For any of the conditions above detected by the analysis circuit 150, in some embodiments the monitoring system 140 can also provide the user 200 with the option to call a dental or orthodontic professional to help the user 200 address the issue if it cannot be addressed by wearing additional aligners, or the system can provide an alert to a dental or orthodontic professional, and the alert can include the photographs or videos of the user used to detect the condition. In some embodiments, the monitoring system 140 may notify the user 200 that the aligner manufacturer will provide the user 200 with new aligners to address the problem. For example, if the analysis circuit 150 determines that a tooth of the user 200 is erupting ectopically, the monitoring system 140 may provide the most recent photos and/or scans to the aligner fabrication center 162 such that a new aligner (or set of aligners) can be created and provided to the user 200 to move the ectopically erupted tooth to the correct location.

In another example, the analysis circuit 150 is configured to measure and/or identify the teeth of the user based on the photos and/or scans provided. The measurements can be based on different landmarks identified on the teeth by the analysis circuit 150. For example, the analysis circuit 150 can measure the height of each tooth (e.g., the vertical distance between the two landmarks spaced furthest apart in a vertical direction), the width of each tooth (e.g., the horizontal distance between the two landmarks spaced furthest apart in a horizontal direction), find the centroid and area of each tooth, and measure the overall size of the upper and lower arches.

At 1222, photos from one or more social media accounts of the user 200 are received. As described, the monitoring application may prompt the user 200 to provide a username and password for each of the social media accounts for the user 200. After the user provides the information to the monitoring application, the monitoring application can access the social media accounts of the user 200 and access the photos posted to the accounts of the user 200. The photos from the social media accounts are downloaded and stored on the memory 146 for further analysis by the analysis circuit 150. As the photos are downloaded and stored, the photos are tagged with the date and time at which the photos were uploaded to the social media accounts. In some embodiments, the monitoring application continuously monitors the social media accounts and downloads photos as they are uploaded to the social media accounts. In some embodiments, the monitoring application accesses the social media sites only when the user 200 opens the monitoring application.

At 1224, the photos are analyzed and compared based on chronology. For example, the analysis circuit 150 compares the photos on the social media accounts of the user 200 to each other in chronological order. To determine the chronological order of the photos, the analysis circuit 150 may read the data associated with the photos to determine when each photo was taken. Data associated with the photos may include a date stamp (e.g., the date on which the photo was taken), a time stamp (e.g., the date and/or time on which the photo was taken), a file name, or additional data within the photo itself indicative of a date and/or time. For example, a photo may include images of a birthday party of the user 200 with an image of a sign that says "Happy $25^{th}$ Birthday." In another example, the analysis circuit 150 can analyze a string of text accompanying a photograph to determine a date of the photograph. For example, the analysis circuit 150 can determine that a photograph of a user was taken the third or fourth week of November if text accompanying the photograph states "Happy Thanksgiving" or includes the keyword "Thanksgiving". The text accompanying the photograph may be part of a social media post that includes or references the photograph of the user. The analysis circuit 150 may determine, based on the age and birthdate of the user 200, when the photo was taken. Furthermore, the analysis circuit 150 may determine when a photo was taken by comparing a photo with an unknown date and/or time to one or more groups of photos with a known date and/or time. For example, a photo with an unknown date and/or time may include an image of the user 200 with a group of people at a certain location. The analysis circuit 150 may search for other images including the same group of people with a known date and/or time to determine if the photo with the unknown date and/or time was taken at approximately the same time or on approximately the same date as the photos with the know date and/or time.

The analysis circuit 150 is equipped with facial recognition software to identify the user 200 in the available photos. The analysis circuit 150 may also compare the photos to the treatment plan. For example, the analysis circuit 150 may group a number of photos of the user from a particular day such that the analysis circuit 150 may analyze the user's teeth in the group of photos. From the group of photos, the analysis circuit 150 may create a model of the user's teeth from the particular day on which the photos were taken. The analysis circuit 150 may then compare the model of the user's teeth generated from the photos to the 3D models used to generate the treatment plan to determine the progress of the user. In some embodiments, the analysis circuit 150 may determine that more data is needed to determine the progress of the user (e.g., additional tooth anatomy, bite registration, a dental classification, etc.), and further determine whether a potential customer can start treatment or whether a current customer can continue or end treatment. In such embodiments, the analysis circuit 150 may communicate with the social media system 190 and prompt the social media system 190 to provide additional images from which the analysis system 150 may analyze additional data to reach a decision.

At 1226, the smile characteristics of the user over time are determined. For example, after identifying the user 200 in the available photos, the analysis circuit 150 identifies the smile on the face of the user 200 in the photos. The smile can be identified by denoting the landmarks of the lips of the user 200 and the teeth of the user 200 in cases where the user is smiling and showing his/her teeth. The smile can also be identified by denoting the corners of the lips in cases where the user is smiling and not showing his/her teeth. The analysis circuit 150 can determine a height of the smile of the user 200 by determining the amount of space between the lips of the user 200 in a photo. The analysis circuit 150 can determine a width of the smile of the user 200 by determining the distance between the corners of the mouth of the user 200. In some embodiments, the analysis circuit 150 assigns a score to each smile identified on each photo, with a higher score corresponding to a larger smile (e.g., a smile with large height and width dimensions). The scores assigned by the analysis circuit 150 can be tagged to the photo stored in the memory 146. The analysis circuit 150 can then determine how the smile of the user 200 has changed over time. For example, the analysis circuit 150 may determine that, since beginning treatment, the smile of the user 200 has increased in height and width, indicating that the user is more confident in his/her smile.

At 1228, the smile characteristics are displayed to the user. For example, the smile characteristics can be displayed to the user via the display 402 and include changes in height, width, and smile frequency (e.g., how much more the user 200 is smiling in recent photos as compared to photos uploaded before treatment or earlier in treatment).

It is important to note that the construction and arrangement of the systems, apparatuses, and methods shown in the various exemplary embodiments is illustrative only. Additionally, any element disclosed in one embodiment may be incorporated or utilized with any other embodiment disclosed herein. For example, any of the exemplary embodiments described in this application can be incorporated with any of the other exemplary embodiment described in the application. Although only one example of an element from one embodiment that can be incorporated or utilized in another embodiment has been described above, it should be appreciated that other elements of the various embodiments may be incorporated or utilized with any of the other embodiments disclosed herein.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

References herein to the positions of elements (e.g., "top," "bottom," "above," "below") are merely used to describe the orientation of various elements in the Figures. It should be noted that the orientation of various elements may differ according to other exemplary embodiments, and that such variations are intended to be encompassed by the present disclosure.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

As utilized herein, the term "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general-purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data that cause a general-purpose computer, special purpose computer, or special purpose processing machines to perform a certain function or group of functions.

What is claimed is:

1. A monitoring system comprising:
   a communications circuit configured to receive an image of a user from a social media system, and to receive orthodontic treatment plan data associated with the user from an aligner fabrication computer system; and
   an analysis circuit configured to:
      determine an actual oral condition of the user at a first time, the first time corresponding to when the image of the user was taken;
      determine a first expected oral condition of the user at the first time based on the orthodontic treatment plan data;
      compare the actual oral condition with the first expected oral condition;
      compare the actual oral condition with (i) a second expected oral condition of the user at a second time based on the orthodontic treatment plan data, the second time occurring before the first time and after the user begins an orthodontic treatment plan, and (ii) a third expected oral condition of the user at a third time based on the orthodontic treatment plan data, the third time occurring after the first time and before the user finishes the orthodontic treatment plan; and
      generate an output based on the comparisons, the output indicative of a progress of the user in relation to the first expected oral condition at the first time when the image of the user was taken;
   wherein the communications circuit is further configured to communicate the output to at least one of a user device and the aligner fabrication computer system;
   wherein the orthodontic treatment plan data comprises a plurality of treatment plan models used to manufacture dental aligners for the user to reposition at least one tooth of the user; and
   wherein the plurality of treatment plan models comprise an initial tooth model, an intermediate tooth model, and a final tooth model, the initial tooth model representing an initial position of the teeth during an orthodontic treatment plan, the intermediate tooth model representing an intermediate position of the teeth during the orthodontic treatment plan, the final tooth model representing a final position of the teeth during the orthodontic treatment plan.

2. The system of claim 1, wherein the analysis circuit is configured to:
   determine the first time by reading time data associated with the image; and
   compare the time data and the orthodontic treatment plan data, the orthodontic treatment plan data including the first expected oral condition, the second expected oral condition, and the third expected oral condition.

3. The system of claim 2, wherein the time data comprises a text string associated with the image identifying when the image was taken.

4. The system of claim 1, wherein the analysis circuit is configured to identify a first tooth landmark in the orthodontic treatment plan data, and wherein the analysis circuit is configured to identify a second tooth landmark in the image, the second tooth landmark corresponding to the first tooth landmark.

5. The system of claim 4, wherein the analysis circuit is configured to compare a position of the first tooth landmark to a position of the second tooth landmark.

6. The system of claim 5, wherein the analysis circuit is configured to determine, based on comparing the position of the first tooth landmark to the position of the second tooth landmark, a treatment plan model of the plurality of treatment plan models that a current configuration of the teeth of the user best represents.

7. The system of claim 6, wherein the analysis circuit is configured to generate a progress status of the user based on a comparison of the current configuration of the teeth of the user to the final tooth model, and wherein the output comprises the progress status.

8. The system of claim 1, wherein the image is a selfie image taken by the user.

9. A method comprising:
receiving, by a communications circuit, an image of a user from a social media system;
receiving, by the communications circuit, orthodontic treatment plan data associated with the user from an aligner fabrication computer system;
determining, by an analysis circuit, an actual oral condition of the user at a first time, the first time corresponding to when the image of the user was taken;
determining, by the analysis circuit, a first expected oral condition of the user at the first time based on the orthodontic treatment plan data;
comparing, by the analysis circuit, the actual oral condition with the first expected oral condition;
comparing, by the analysis circuit, the actual oral condition with (i) a second expected oral condition of the user at a second time based on the orthodontic treatment plan data, the second time occurring before the first time and after the user begins an orthodontic treatment plan, and (ii) a third expected oral condition of the user at a third time based on the orthodontic treatment plan data, the third time occurring after the first time and before the user finishes the orthodontic treatment plan;
generating, by the analysis circuit, an output based on the comparison, the output indicative of a progress of the user in relation to the first expected oral condition at the first time the image of the user was taken; and
communicating, by the communications circuit, the output to at least one of a user device and the aligner fabrication computer system;
wherein the orthodontic treatment plan data comprises a plurality of treatment plan models used to manufacture dental aligners for the user to reposition at least one tooth of the user; and
wherein the plurality of treatment plan models comprise an initial tooth model, an intermediate tooth model, and a final tooth model, the initial tooth model representing an initial position of the teeth during an orthodontic treatment plan, the intermediate tooth model representing an intermediate position of the teeth during the orthodontic treatment plan, the final tooth model representing a final position of the teeth during the orthodontic treatment plan.

10. The method of claim 9, the method further comprising:
determining, by the analysis circuit, the first time by reading a time data associated with the image; and
comparing, by the analysis circuit, the time data and the orthodontic treatment plan data, the orthodontic treatment plan data including the first expected oral condition, the second expected oral condition, and the third expected oral condition.

11. The method of claim 10, wherein the time data comprises a text string associated with the image identifying when the image was taken.

12. The method of claim 9, further comprising:
identifying, by the analysis circuit, a first tooth landmark in the orthodontic treatment plan data; and
identifying, by the analysis circuit, a second tooth landmark in the image, the second tooth landmark corresponding to the first tooth landmark.

13. The method of claim 12, further comprising comparing, by the analysis circuit, a position of the first tooth landmark to a position of the second tooth landmark.

14. The method of claim 13, further comprising determining, by the analysis circuit based on comparing the position of the first tooth landmark to the position of the second tooth landmark, a treatment plan model of the plurality of treatment plan models that a current configuration of the teeth of the user best represents.

15. The method of claim 14, further comprising generating, by the analysis circuit, a progress status of the user based on a comparison of the current configuration of the teeth of the user to the final tooth model, wherein the output comprises the progress status.

16. The method of claim 9, wherein the image is a selfie image taken by the user.

17. The system of claim 1, wherein the communications circuit is configured to access a social media account of the user.

18. The system of claim 17, wherein the communications circuit is configured to receive a username and a password related to the social media account of the user to access the social media account of the user.

19. The system of claim 17, wherein the communications circuit is permitted to access the social media account of the user continuously.

20. The system of claim 17, wherein the communications circuit is configured to download the image from the social media account of the user, the image including data related to at least one of a date when the image was taken, the first time, a date when the image was uploaded to the social media account, a fourth time corresponding to when the image was uploaded to the social media account, a name associated with the image, or an account number associated with the image.

21. The system of claim 17, wherein the communications circuit is configured to download the image from another social media account than the social media account of the user, wherein the user is tagged in the image from the another social media account, the image from the another social media account including data related to at least one of a date when the image was taken, the first time, a date when the image was uploaded to the social media account, a fourth time corresponding to when the image was uploaded to the social media account, a name associated with the image, or an account number associated with the image.

22. The system of claim 17, wherein the communications circuit is configured to access the social media account of the user via the user device.

23. The system of claim 17, wherein the communications circuit is permitted to access the social media account of the user for a predetermined period of time.

* * * * *